United States Patent [19]
Robinson et al.

[11] Patent Number: 5,476,664
[45] Date of Patent: Dec. 19, 1995

[54] TREATMENT OF WARTS USING ANTHRALINS AND OCCLUSION

[75] Inventors: Howard N. Robinson, Lutherville; Neil F. Martin, Potomac, both of Md.

[73] Assignees: Leonard Bloom, Towson; Marvin S. Townsend, Rockville, both of Md.; a part interest

[21] Appl. No.: 228,130

[22] Filed: Apr. 15, 1994

[51] Int. Cl.$^6$ .................................................. A61F 13/00
[52] U.S. Cl. .................... 424/443; 424/447; 424/448; 424/489; 514/938
[58] Field of Search .................................. 424/443, 447

[56] References Cited

U.S. PATENT DOCUMENTS

| | | | |
|---|---|---|---|
| 4,073,291 | 2/1981 | Marvel | 128/155 |
| 4,465,688 | 8/1984 | Shroot | 514/410 |
| 4,495,203 | 1/1985 | Grollier | 514/732 |
| 4,504,494 | 3/1985 | Grollier | 514/544 |
| 4,588,590 | 5/1986 | Bernstein | 424/195.1 |
| 4,696,941 | 9/1987 | Shroot | 514/423 |
| 4,866,095 | 9/1989 | Shroot | 514/569 |
| 5,017,587 | 5/1991 | Montes | 514/328 |
| 5,093,360 | 3/1992 | Yu | 514/463 |

OTHER PUBLICATIONS

Seville et al, "Dithranol cream", British Journal of Dermatology, (1979), vol. 100, pp. 475–476.
Wilson et al, "Dithrocream in psoriasis", British Journal of Dermatology, (1980), vol. 102, pp. 105–106.
Eriksen, "Treatment of the Common Wart by Induced Allergic Inflammation", Dermatologica, vol. 160, (1980), pp. 161–166.
De Groot et al, "Contact allergy to dithranol" in Contact Dermatitis, vol. 7, pp. 5–8, 1981.
Whitefield, "Pharmaceutical formulations of anthralin", in British Journal of Dermatology, (1981), vol. 105, Supplement 20, pp. 28–32.
*The Merck Index, Tenth Edition,* (1983) for the entry "Anthralin".

Ashton et al entitled "Anthralin: Historical and Current Perspectives" in the Journal of the American Academy of Dermatology, vol. 9, No. 2, Aug. 1983, pp. 173–191.
Franceschi et al, "Genital warts and cervical neoplasia: An epidemiological study", Br. J. Cancer, vol. 48, pp. 621–628, (1983).
Crum et al, "Human papillomavirus Type 16 and Early Cervical Neoplasia", The New England Journal of Medicine, vol. 310, No. 14, pp. 880–883, (Apr. 5, 1984).
Flindt–Hansen et al, "Wart Treatment With Anthralin", in Acta. Derm. Venereol. (Stockh.) 64: 177–180, 1984.
Lowe et al entitled "Anthralin for psoriasis: Short–contact anthralin therapy compared with topical steroid and conventional anthralin", in Journal of the American Academy of Dermatology, vol. 10, No. 1, pp. 69–72, Jan. 1984.
A brochure published by Dermik Laboratories, Inc. entitled "Anthralin Therapy Simplified", that accompanies the Drithocreme (™) product, includes text of a letter written by Nicholas J. Lowe, M.D., the same Dr. Lowe who coauthored the above–mentioned article.

(List continued on next page.)

*Primary Examiner*—D. Gabrielle Phelan
*Attorney, Agent, or Firm*—Leonard Bloom; Marvin S. Towsend

[57] ABSTRACT

A method of treating a patient having one or more warts includes the steps of: applying to the wart an amount of a composition consisting essentially of an anthralin active ingredient and a pharmaceutical carrier; covering the wart and skin areas peripheral to the wart with an adhesive tape, such that the adhesive tape adheres to peripheral skin areas, whereby the adhesive tape provides an occluding environment for the wart treated with the composition. The occluding environment is maintained for a desired period of time, and the adhesive tape is removed. For a number of times as desired, a fresh amount of anthralin-containing composition is applied, and a fresh piece of adhesive tape is applied to recreate the occluding environment.

39 Claims, 3 Drawing Sheets

OTHER PUBLICATIONS

Hjorth et al entitled "Anthralin Stick (Anthraderm) in the Treatment of Mosaic Warts", in Acta. Derm. Venereol. (Stockh.) 66: 181–182, 1986.

Mare et al, "Dithranol in the Treatment of Inflammatory Linear Verrucous Epidermal Nevus", in Acta Derm Venereol (Stockh), vol. 69 (Short Reports), pp. 77–80, (1989).

Kanerva, "Electron microscopic observations of dyskeratosis, apoptosis, colloid bodies and fibrillar degeneration after skin irritation with dithranol", in J. Cutan. Pathol., vol. 17, pp. 37–44, 1990.

Rulo et al. "Treatment of Inflammatory Linear Verrucous Epidermal Nevus", Dermatologica, 1991, vol. 182, pp. 112–114.

Vance, *"Verruca Vulgaris* (Warts)", pp. 743–745, in Conn's Current Therapy 1992, edited by Robert E. Rakel, M.D., W. B. Saunders Company, (1992).

Gottlieb et al entitled "Anthralin Decreases Keratinocyte TGF–alpha Expression and EGF–Receptor Binding in Vitro", in The Journal of Investigative Dermatology, vol. 98, No. 5, May 1992, pp. 680–685.

*Physicians' Desk Reference,* 1993, under a listing for American Dermal Corporation, Plumsteadville, Pennsylvania 18949.

TREATMENT OF WARTS USING ANTHRALINS AND OCCLUSION

FIELD OF THE INVENTION

The present invention relates to the field of treating warts, also known as verruca vulgaris, and more specifically with the topical treatment of warts using treating agents known as anthralins.

BACKGROUND OF THE INVENTION

A wide variety of warts are found on human skin and are caused by the human papilloma virus (HPV). For example, the following types of warts are found on human skin and are caused by the human papilloma virus (HPV): common warts (verruca vulgaris), plantar warts, palmar warts, planar warts (verruca plana), mosaic warts, and venereal warts (condyloma accuminatum). These skin growths are unsightly, irritating, and potentially oncogenic (carcinogenic), and their removal is desired.

Throughout the years a number of therapies have been developed for treating warts, and these therapies can be categorized in the following seven categories: (1) locally destructive chemicals; (2) surgically destructive methods; (3) blister-producing methods; (4) cellular inhibition; (5) altering the cutaneous environment; (6) immune stimulation; and (7) miscellaneous methods. See the article by Vance entitled "Verruca Vulgaris (Warts)", pages 743–745, in Conn's Current Therapy 1992, edited by Robert E. Rakel, M.D., W. B. Saunders Company, (1992).

Treatment methods using locally destructive chemicals include using the following chemicals: salicylic acid (in films, plasters, pads, and tapes); lactic acid; trichloracetic acid (TCA); bichloroacetic acid (BCA); nitric acid; and glacial acetic acid.

Surgically destructive methods include the following techniques: excision; electrocautery; electrodesiccation; curettage; blunt dissection; and laser vaporization or coagulation.

Blister-producing methods include the following techniques: liquid nitrogen cryotherapy; carbon dioxide cryotherapy; and cantharidin.

Cellular inhibition methods include use of the following agents: podophyllin and podophyllotoxin; 5-fluorouracil; bleomycin; colchicine; interferon local injections; and radiation.

Methods for altering the cutaneous environment include the following agents or techniques: retinoids; formalin; glutaraldehyde; aluminum chloride; and heat therapy.

Immune stimulation methods of treatment include the following: dinitrochlorobenzene (DNCB); interferon systemic injections; and vaccination, autologous or intralesional.

Miscellaneous methods include: hypnosis; and tape occlusion. On page 745 of the Vance article, there is a statement that hypnosis and tape occlusion probably have a placebo effect providing an about 20% cure.

Currently, there are a number of over-the-counter products on the market that are used for treating warts. One such product is Pedia Patch (TM) of Tsumura International, Inc., Shakopee, Minn. 55379. This product contains a quantity of salicylic acid in a sticky base. The salicylic acid/sticky base is retained and carried by a piece of adhesive tape. In use, the salicylic acid/sticky base is applied to the wart, and free ends of the adhesive tape are applied to peripheral skin areas to keep the treating agent in place on the skin. This product employs two of the above-mentioned seven wart treatment methods simultaneously, namely: (1) a locally destructive chemical (salicylic acid); and (7) tape occlusion.

A second over-the-counter wart treatment product is Duo Plant (R) a plantar wart removal system of Schering Plough, Healthcare Products, Inc., Memphis, Tenn. 38151. This product is a gel that includes alcohol 57.6% w/w, ether 16.42% w/w, ethyl lactate, hydroxypropyl cellulose, and polybutene in flexible collodion. The gel is applied directly to the wart, and the solvents evaporate leaving a film with treating agent.

A third over-the-counter wart treatment product is Dr. Scholls Clear Away Plantar Wart Remover System (TM) of Schering Plough Healthcare Products, Inc., Memphis, Tenn. This product includes adhesive-tape-containing discs which contain salicylic acid (40%) in a rubber-based vehicle. The salicylic acid/rubber base is retained and carried by the piece of adhesive tape. In use, the salicylic acid/rubber base is applied to the wart, and free ends of the adhesive tape are applied to adjacent skin areas to keep the treating agent in place on the skin. This product employs two of the above-mentioned seven wart treatment methods simultaneously, namely: (1) a locally destructive chemical (salicylic acid); and (7) tape occlusion.

A fourth over-the-counter wart treatment product is Compound W (TM) of Whitehall Laboratories, Inc., New York, N.Y. 10017. The active ingredient in the product is salicylic acid (17% w/w). Inactive ingredients in the product include: acetone; collodion; alcohol (2.2% w/w); camphor; castor oil; ether (63.5%); menthol; and Polysorbate 80. In use, this product is applied as a liquid coating to a wart. When the solvents evaporate, the wart is covered by a flexible film which contains the active ingredient.

Fifth and sixth over-the-counter wart treatment products are Transplantar (TM) and Transversol (TM), respectively, made by Bradley Pharmaceutical Co., 383 Route 46 West, Fairfield, N.J. 07004. Each of these products employs salicylic acid in a gum base. A piece of adhesive tape retains and carries the salicylic acid/gum base composition. In use, the salicylic acid/gum base composition is placed over the wart, and the adhesive tape is applied to adjacent skin to keep the device in position. This product employs two of the above-mentioned seven wart treatment methods simultaneously, namely: (1) a locally destructive chemical (salicylic acid); and (7) tape occlusion.

Another wart treatment product is Occlusal-HP (TM), by Gen Derm Corporation, Lincolnshire, Ill. 60069. It is noted that Occlusal HP contains 17% salicylic acid in a polyacrylic vehicle containing ethyl acetate, isopropyl alcohol, butyl acetate, polyvinyl butyral, dibutyl phthalate, acrylates copolymer, and nitrocellulose. The pharmacologic activity of Occlusal-HP is generally attributed to the keratolytic action of salicylic acid which results in mechanical removal of epidermal cells infected with wart viruses.

Another wart treatment product is a plaster called Sal-Acid Plaster (TM) by Pedinol Pharmacal, Inc., 30 Banfi Plaza, Farmingdale, N.Y. 11735. This product contains 40% salicylic acid.

Yet another wart treatment product is disclosed in the 1990 edition of the Physicians Desk Reference (PDR), published by Medical Economics Data Production Company, Montvale, N.J. This wart treatment product is Viranol (TM) gel made by American Dermal Corp., Bedminster Industrial Park, P.O. Box 900, Plumsteadville, Pa. 18949.

Viranol gel has 12% salicylic acid as its active ingredient.

Aside from the treatments mentioned above which have attained the status of generally accepted methods and techniques in medical practice for treating warts, there are publications in the literature which disclose still other methods and techniques for treating warts. Of special relevance with respect to the present patent are publications which disclose anthralin or its analogs or derivatives in the treatment of warts.

Anthralin is also known as dithranol, and its chemical name is 1,8-dihydroxy-9(10H)-anthracenone. An alternate chemical name for anthralin is 1,8-dihydroxyanthrone. Still another accepted chemical name for anthralin is 1,8-dihydroxy,9-anthrone. Commercial preparations containing anthralin include Anthra-Derm, Antraderm, Batidrol, Cignolin, Cigthranol, Drithocreme, Psoradrate, and Psoriacide. The triacetate is known as 1,8,9-anthracenetriol triacetate and, alternatively, as 1,8,9-triacetoxyanthracene, which is known commercially as Exolan. See *The Merck Index, Tenth Edition*, (1983) for the entry "Anthralin".

In an article by Flindt-Hansen et al entitled "Wart Treatment With Anthralin", in Acta. Derm. Venereol. (Stockh.) 64: 177–180, 1984, there is a disclosure that 27 patients were treated with Anthraderm (2% anthralin and 0.5% salicylic acid in a wax preparation enclosed in a lipstick-like container). More specifically, the treatment involved application of the Anthraderm twice a day by the patients. Every 2 weeks gentle cutting and scraping of the warts were performed in a clinic. Undergoing this treatment of topical application of Anthraderm and periodic cutting and scraping, 15 (56%) of the 27 patients were cured; that is, no wart tissue was visible. There is a teaching that in psoriasis, the effect of anthralin is thought to consist in a reduction of the cell turn over caused by an inhibition of the cell metabolism. These pharmacological effects in the cell metabolism might be beneficial in the treatment of the benign tumour produced by replicating wart virus. There is no disclosure that any tape occlusion was used.

In an article by Hjorth et al entitled "Anthralin Stick (Anthraderm) in the Treatment of Mosaic Warts", in Acta. Derm. Venereol. (Stockh.) 66: 181–182, 1986, there is a disclosure that anthralin in a wax-based stick (2% anthralin stick) that was used for 2 months was effective against common warts. More specifically, there were 30 patients treated. After a mean of 7 months of treatment (range, 3 to 10 months), warts in 17 patients were cleared, and warts in 7 patients persisted. The remaining 6 patients dropped out. The treatment involved daily application of 2% anthralin stick supplemented by weekly paring (cutting or shaving) of the wart. By having 17 patients out of 30 patients cleared of warts, the percentage of patients cleared of warts is 57%. There is no disclosure that any tape occlusion was used.

In an article by Mare et al entitled "Dithranol in the Treatment of Inflammatory Linear Verrucous Epidermal Nevus" in Acta Derm Venereol (Stockh), Vol. 69 (Short Reports), pages 77–80, (1989), there is a disclosure that dithranol (also known as anthralin) was used to treat a patient with the short contact anthralin therapy (SCAT) method to treat the psoriasis condition known as inflammatory linear verrucous epidermal nevus (ILVEN). Over an 8 week period, the concentration of the anthralin was increased in the following increments in the short contact anthralin therapy (SCAT) method: 0.5%, 1%, 2%, 3%, 4%, and 5%. There is no disclosure that the anthralin was used in treating common warts. There is no disclosure that any tape occlusion was used.

By and large, anthralin is used primarily in the treatment of psoriasis. Psoriasis is a condition of the skin in which skin cells mature abnormally rapidly resulting in increased cellular turnover and rapid growth of the skin. There is no involvement of the human papilloma virus (HPV) in psoriasis. Aside from anthralin, other conventional treatments for psoriasis include topical corticosteroids, tar, UV-B radiation, psoralens and UV-A radiation, and bland emollients.

More specifically with respect to the treatment of psoriasis, the following U.S. patents discloses compositions containing anthralin or its derivatives or analogs for treating psoriasis: U.S. Pat. Nos. 4,465,688; 4,495,203; 4,504,494; 4,696,941; and 4,866,095. More specifically, in U.S. Pat. No. 4,465,688, from column 13, line 49 to column 14, line 2, a composition is disclosed which contains 9,10-dihydro-1,8,9-trihydroxy-9,10-anthracene-alpha,beta-endo-N-ethyl succinimide (a compound related to anthralin) approximately 1.47% by weight; salicylic acid, approximately 0.68% by weight; and petroleum jelly, approximately 97.85% by weight. The composition is prepared in the form of a suspension that is applied once a day for three weeks. Excellent results are obtained on the psoriasis areas very similar to those obtained with anthralin but with no primary irritation and without staining of the skin. In this patent there is a nominal disclosure that warts can also be treated with the 9,10-dihydro-1,8,9-trihydroxy-9,10-anthracene-alpha,beta-endo-N-ethyl succinimide, but no specific protocol for treating warts is disclosed. In this respect, there is no disclosure that any tape occlusion is used for treating warts with the 9,10-dihydro-1,8,9-trihydroxy-9,10-anthracene-alpha,beta-endo-N-ethyl succinimide. U.S. Pat. No. 4,866,095 has disclosures similar to U.S. Pat. No. 4,465,688.

U.S. Pat. No. 4,504,494 discloses that anthralin compositions are used in the treatments of psoriasis and warts. In this patent, Examples IV, VII, VIII, XIII, and XIV disclose compositions which contain anthralin and an aromatic ester vehicle. Some of the examples also contain a solid material such as silica. The patent gives special emphasis to the treatment of psoriasis. There is no specific disclosure on the treatment of warts with anthralin. Also, there is no disclosure that any tape occlusion is used. U.S. Pat. No. 4,495,203 has disclosures similar to U.S. Pat. No. 4,504,494.

U.S. Pat. No. 4,696,941 discloses compounds related to anthralin that are used in the treatment of psoriasis, acne, warts, and rheumatism. Treatment of psoriasis, acne, and warts is by topical treatment. Treatment of rheumatism is by injection. Examples 9–18 disclose topically administrable compositions. There is no specific example of treatment of warts. Also, there is no disclosure that any tape occlusion is used.

Additional publications relating to the use of anthralin to treat psoriasis are discussed below.

In an article by Gottlieb et al entitled "Anthralin Decreases Keratinocyte TGF-alpha Expression and EGF-Receptor Binding in Vitro", in The Journal of Investigative Dermatology, Vol. 98, No. 5, May 1992, pages 680–685, there is a disclosure that anthralin is an effective topical treatment for active psoriasis. It is suggested that pharmacologically relevant concentrations of anthralin have the ability to strongly inhibit keratinocyte proliferation in vitro, possibly by affecting early steps in mitogenic signalling pathways. Anthralin diminishes ligand binding to the epidermal growth factor (EGF) receptor via a reduction in binding affinity. There are teachings that anthralin treatment has been reported to inhibit granulocyte function, inhibit the lipoxygenase pathways, inhibit DNA replication and repair, inhibit mitochondrial respiration, and decrease calmodulin activity in vitro. In vivo, anthralin decreases plasminogen activator levels in plaques, inhibits mitochondrial ATP synthesis, and normalizes keratin expression. There is no disclosure of any treatment methods that employ anthralin that make use of an irritant response generated by anthralin. In this article, there is no disclosure of the use of anthralin in treating warts. Moreover, there is no disclosure that any occlusion device was used.

In an article by Ashton et al entitled "Anthralin: Historical and Current Perspectives" in the Journal of the American Academy of Dermatology, Volume 9, Number 2, August 1983, pages 173–191, there is an extensive review of the uses of anthralin therapy. The only medical condition discussed in the entire article that is treated with anthralin is psoriasis. There is no mention whatsoever of the use of anthralin to treat warts. On pages 187–188, there are recommendations for the use of anthralin in treating psoriasis. Since anthralin has the immediate side effects of skin irritation and staining, its use should be closely monitored. In essence, the irritant effects of anthralin are to be avoided in the treatment of psoriasis. Anthralin is administered in the form of the commercially available Drithocreme (TM).

In the *Physicians' Desk Reference*, 1993, under a listing for American Dermal Corporation, Plumsteadville, Pa. 18949, Drithocreme (TM) is disclosed to be comprised of anthralin (approximately 0.1%, 0.25%, 0.5%, or 1%) in a base of white petrolatum, sodium lauryl sulfate, cetostearyl alcohol, ascorbic acid, salicylic acid, chlorocresol, and purified water.

In the Ashton et al article, In Table II on page 187, there are suggested guidelines for home use of anthralin cream (Drithocreme(TM)) or ointment (Anthra-Derm(TM)) in the treatment of psoriasis. The guidelines suggest that anthralin should start a 0.1% and increase to 0.25%, 0.5%, and 1%. The treatment should continue for 1 to 2 weeks with this step-wise increase in the strength of the anthralin. The stepwise increase in the concentration of the anthralin used is to avoid skin irritation; that is, to avoid an irritant response. Moreover, on page 188, there is a suggestion that "short contact therapy" may be a practical outpatient therapy for the future.

It is noted that Drithocreme (TM) described in the *Physicians' Desk Reference* listing for American Dermal Corporation, Plumsteadville, Pa. 18949 is currently a product of Dermik Laboratories, Inc., Collegeville, Pa. Drithocreme (TM) is available in four concentrations (approximately 0.1%, 0.25%, 0.5%, and 1%[HP]) for the treatment of psoriasis. In literature published by Dermik Laboratories for using Drithocreme (TM), it is recommended that the 0.1% strength anthralin formulation of Drithocreme (TM) be used for at least one week to assess each patient's individual tolerance to anthralin.

In an article by Lowe et al entitled "Anthralin for psoriasis: Short-contact anthralin therapy compared with topical steroid and conventional anthralin", in Journal of the American Academy of Dermatology, Vol. 10, No. 1, pages 69–72, January 1984, there is a disclosure that conventional overnight (approximately 8 hours) anthralin therapy for psoriasis uses anthralin in a range of 0.1%–0.5% anthralin. On page 70 there is a statement that no higher concentration than 0.5% was used in conventional anthralin therapy for psoriasis, as higher concentrations in petrolatum would be irritating if left on overnight. It is clear that in the treatment of psoriasis, the irritant effects of anthralin are to be avoided. On the other hand, higher anthralin concentrations, in the range of 0.5%–3%, are left on for 10 minutes and then washed off with soap and hot water. With this short contact anthralin therapy, the initial concentration of anthralin was 0.5%, and this was increased to 1% and 3% at 3-day intervals. A key objective of the short contact anthralin therapy is to avoid an irritant response to anthralin.

A brochure published by Dermik Laboratories, Inc. entitled "Anthralin Therapy Simplified", that accompanies the Drithocreme (TM) product, includes text of a letter written by Nicholas J. Lowe, M.D., the same Dr. Lowe who coauthored the above-mentioned article. The Lowe letter discloses that Drithocreme (TM) can also be used for short contact anthralin therapy (SCAT) for treating psoriasis without causing skin irritation. The SCAT method of treating psoriasis is employed with a key intended purpose of avoiding an irritant/immunologic response to anthralin. The recommended dosage and contact time for Drithocreme (TM) is Drithocreme (TM) containing 1% anthralin for 10 minutes. However, under certain circumstances, short contact anthralin therapy can be employed up to 60 minutes. There is no disclosure of the use of any concentration of Drithocreme (TM) for treating warts. In addition, there is no disclosure that Drithocreme (TM) any tape occlusion was used.

In an article by De Groot et al entitled "Contact allergy to dithranol" in Contact Dermatitis, Vol. 7, pages 5–8, 1981, there is a disclosure that a patient having common warts on the hands was treated with collodion containing dithranol 3%, salicylic acid 25%, and acetone 10%. After two applications, the patient had stopped the treatment because she experienced itching and noticed small blisters on the her hands. Examination of the patient showed a systemic response; that is, there were papulovesicular eczematous lesions on both arms, legs, and abdomen. The hands showed an oozing vesicular dermatitis, the warts being swollen. The eczematous reaction subsided with topical steroid medication in a couple of days. After running a series of patch tests, it was determined that the patient was allergic to dithranol. Three weeks after two applications of the collodion containing the dithranol 3%, salicylic acid 25%, and acetone 10%, all warts had completely cleared. The authors theorized that the curing of the warts in the patient was probable attributable to the contact allergic dermatitis induced by dithranol. This patient was a relatively rare person who had a contact dermatitis to dithranol. There is no suggestion in the article that most patients, not having a systemic allergic response to dithranol, are to be treated with dithranol to elicit an irritant response in the treatment of warts. In this article, there is also a disclosure that patients suffering from the condition known as alopecia areata were simultaneously treated with dithranol and 2,4-dinitrochlorobenzene (DNCB) wherein the DNCB is a known immuno-stimulating agent. As a result, these patients had a contact allergy to dithranol. There is no disclosure that tape occlusion was employed in any of the treatment methods.

In an article by Kanerva entitled "Electron microscopic observations of dyskeratosis, apoptosis, colloid bodies and fibrillar degeneration after skin irritation with dithranol", in J. Cutan. Pathol., Vol. 17, pages 37–44, 1990, there is a disclosure that healthy skin on the backs of volunteers was treated with dithranol using the epicutaneous Finn chamber occlusion technique. The dithranol concentrations used were 0.2% dithranol in petrolatum and 0.1% dithranol in petrolatum. The results were the observations, under the electron microscope, of dyskeratosis, apoptosis, colloid bodies and fibrillar degeneration after skin irritation of the healthy skin with dithranol. There is a statement on page 37 that cellmediated immunity is believed to play an important role in regression (not treatment) of plane warts. On page 43, there is a statement that immunocompetent lymphocytes are seen under the electron microscope to be apposed to Langerhans cells (LC) after dithranol irritation. In the article, dithranol is referred to as an anti-psoriatic drug, and there is no mention of the treatment of warts in this article. Also, there is no mention of the use of tape occlusion.

As stated above, warts are caused by the human papilloma virus (HPV). There are findings reported in the literature that human papilloma virus may be implicated in certain forms of cancer See Franceschi et al, "Genital warts and cervical neoplasia: An epidemiological study", Br. J. Cancer, Vol. 48, pages 621–628, (1983) and Crum et al, "Human papillomavirus Type 16 and Early Cervical Neoplasia", The New England Journal of Medicine, Vol. 310, No. 14, pages 880–883, (Apr. 5, 1984). In view of the link between the human papilloma virus and cancer, the prompt and effective treatment and destruction of warts is strongly indicated.

Upon reviewing the prior art cited above, certain conclusions can be made about the prior art as a whole. First, none of the prior art discloses the use of an anthralin with tape occlusion to treat warts. Second, the prior art treatments of warts which do involve tape occlusion include only solid materials such as solid salicylic acid. Third, tape occlusion for treating warts is not disclosed as being used with a liquid or pasty material.

A fourth conclusion that can be made about the prior art is that of the seven techniques for treating warts discussed above (that is: (1) locally destructive chemicals; (2) surgically destructive methods; (3) blister-producing methods; (4) cellular inhibition; (5) altering the cutaneous environment; (6) immune stimulation; and (7) miscellaneous methods), tape occlusion (in technique No. 7) is used in conjunction only with technique No. 1 which involves the locally destructive chemical salicylic acid. Tape occlusion is not used in conjunction with technique Nos. 2–6.

A fifth conclusion that can be made about the prior art is that tape occlusion by itself probably has a placebo effect providing an about a 20% cure.

A sixth conclusion that can be made about the prior art is that the treatment of warts with anthralin without concomitant tape occlusion (as described by Flindt-Hansen et al and Hjorth et al) has resulted in a wart clearing rate no greater than 57%.

A seventh conclusion that can be made about the prior art is that the mode of operation of anthralin in the treatment of warts is thought to consist of a reduction of the replication of the wart virus caused by an inhibition of the cell metabolism.

An eighth conclusion that can be made about the prior art is that immune stimulation methods of wart treatment do not include anthralin as an immune stimulating agent.

A ninth conclusion that can be made about the prior art is that there is no disclosure of any treatment methods employing tape occlusion that make use of an immune response generated by an active ingredient. As a corollary conclusion, there is no disclosure of any wart treatment methods employing tape occlusion that make use of an immune response generated by anthralin.

A tenth conclusion that can be made about the prior art is that anthralin is employed in the treatment of psoriasis in a manner clearly designed to avoid an undesired immunologic/irritant response to anthralin.

An eleventh conclusion that can be made about the prior art is that when salicylic acid is used with tape or film occlusion for treating warts, the range of salicylic acid is in a range of 17% to 40%. In this respect, it is recalled that in Compound W (TM) of Whitehall Laboratories, Inc., New York, N.Y. 10017, the active ingredient in the product is salicylic acid at 17% w/w. It is also recalled that in the article by De Groot et al entitled "Contact allergy to dithranol" discussed above, there is a disclosure that a patient having common warts on the hands was treated with collodion containing dithranol 3%, salicylic acid 25%, and acetone 10%. It is further recalled that in Dr. Scholls Clear Away Plantar Wart Remover System of Schering Plough Healthcare Products, Inc., Memphis, Tenn., the product includes adhesive-tape-containing discs which contain salicylic acid (40%) in a rubber-based vehicle.

A twelfth conclusion that can be made about the prior art is that when salicylic acid is used to stabilize (acidify) an anthralin, salicylic acid is present in an amount of less than 2.0% by weight. In this respect, it is recalled that in U.S. Pat. No. 4,465,688, from column 13, line 49 to column 14, line 2, a composition is disclosed which contains 9,10-dihydro-1,8,9-trihydroxy-9,10-anthracene-alpha,beta-endo-N-ethyl succinimide (a compound related to anthralin) approximately 1.47% by weight; salicylic acid, approximately 0.68% by weight; and petroleum jelly, approximately 97.85% by weight. It is also recalled that an anthralin ointment employs a pharmaceutical carrier described in the British Pharmacopoeia as Lassar's paste. This carrier includes 240 g. of zinc oxide finely sifted, 20 g. of salicylic acid finely sifted, 240 g. of starch finely sifted, and 500 g. of white soft paraffin. Anthralin ointments containing the Lassar's paste can include anthralin in concentrations ranging from 0.5% to 5.0%. Thus, the percentage of salicylic acid in a Lassar's paste based ointment is less than 2.0% by weight.

A thirteenth conclusion that can be made from the prior art is that a therapeutic amount of salicylic acid for treating warts by tape or film occlusion is equal to or greater than 17% salicylic acid by weight.

A fourteenth conclusion that can be made about the prior art, which is a corollary of the thirteenth conclusion, is that the presence of salicylic acid in a composition for treating warts by tape or film occlusion in an amount less than 17% by weight of the composition is a less than therapeutic amount of salicylic acid for treating the warts.

In forming a fifteenth conclusion, it is recalled that the lowest percentage of salicylic acid in a wart treating composition that is discussed hereinabove is 12% salicylic acid in Viranol gel. From the percentage of salicylic acid in Viranol and from the percentages of salicylic acid in other wart-treating products, it may be concluded that the lowest effective percentage of salicylic acid in a wart treating composition is 12% salicylic acid. It is noted, however, that Vironal gel is not used with tape occlusion.

Considering a prudent 3% margin of error with respect to the 17% therapeutic amount of salicylic acid for tape occlusion for treating warts, it is further concluded, as a sixteenth conclusion, that an amount of less than 14% by weight of salicylic acid for tape occlusion for treating warts is less than a therapeutic amount of salicylic acid for tape occlusion.

Furthermore, considering a prudent 3% margin of error with respect to the 12% therapeutic amount of salicylic acid in Vironal gel for treating warts topically, it is further concluded, in a seventeenth conclusion, that an amount of less than 9% by weight of salicylic acid for treating warts topically (without tape occlusion) is less than a therapeutic amount of salicylic acid for topical treatment of warts.

SUMMARY OF THE INVENTION

Accordingly, it is an object of the invention to provide a method of treating warts that employs the use of an anthralin with tape occlusion.

Another object of the invention is to provide a method of treating warts which employs tape occlusion using a liquid or pasty material.

Still another object of the invention is to provide a method of treating warts which employs tape occlusion in conjunction with blister-producing methods, cellular inhibition, altering the cutaneous environment, or immune stimulation.

Yet another object of the invention is to provide a method of treating warts which results in a wart clearing rate greater than two-thirds.

Another object of the invention is to provide a method of treating warts employing tape occlusion that make use of an immune response generated by an active ingredient.

Even another object of the invention is to provide a method of treating warts in which the mode of operation of anthralin includes anthralin as an immune stimulating agent.

Still another object of the invention is to provide a method of treating warts employing tape occlusion that makes use of an immune response generated by anthralin.

In accordance with the invention, a method is provided for treating a patient (a human being or animal) who has one or more warts. The method includes the steps of (a). applying to a wart an amount of a composition consisting essentially of an anthralin active ingredient in a concentration greater than 0.5% by weight and a pharmaceutical carrier, (b). covering the wart and skin area peripheral to the wart with a tape which provides an occluding environment for the wart, and (c). maintaining the tape in position over the wart and peripheral skin area for a predetermined period, the tape providing an occluding environment for the wart for the predetermined period of time. The predetermined period of time can be in a range spanning 1–18 hours.

In accordance with the invention, the following additional steps can be employed: (d). removing the tape after the predetermined period of time; and repeating the steps (a) through (d) periodically until a desired level of wart removal has been obtained. It is noted that normal periodic hygiene, such as washing with soap and water during a bath, shower, or sink wash up, may take place after a sequence of above steps (a) through (d) and before a repetition of steps (a) through (d).

It is noted that after the tape is removed from the wart, the wart may be pared or scraped or scored. The generic term for paring, scraping, and scoring is debriding. Thus, further in accordance with the invention, the method of treating warts of the invention can further include the step of debriding the wart prior to repeating steps (a) through (d) set forth above.

The pharmaceutical carrier for the anthralin may include an oil base for dissolving and suspending the anthralin, an oil-soluble acidifying agent, an aqueous medium, and a water-soluble antioxidant, such that the pharmaceutical carrier and the anthralin are present in the form of an emulsion, e.g. an oil-in-water emulsion.

In the pharmaceutical carrier, the oil base may be petrolatum; the oil-soluble acidifying agent may be salicylic acid (in an amount less than 12% by weight); the aqueous medium may be purified water; and the water-soluble antioxidant may be ascorbic acid. The emulsion may be a cream. More specifically, the cream may be an oil-in-water emulsion.

The pharmaceutical carrier may also include a surfactant for stabilizing the oil-in-water emulsion. The anthralin may be present in a concentration range spanning 0.50%–1.50% by weight, or more broadly in a concentration ranging from 0.50%–5.0% by weight, or even more broadly in a concentration ranging from 0.50%–10.0% by weight.

More specifically, the anthralin may be present in a concentration range spanning 0.50% to 10.0% by weight, and the predetermined time for tape occlusion is at least 1 hour and may be in a range from 1–18 hours, such as overnight.

The tape used for tape occlusion may be commonly employed adhesive tape such as Johnson and Johnson waterproof adhesive tape or a plastic film (with or without an adhesive layer). In the present patent, the terms tape occlusion and film occlusion are deemed to be equivalent. The plastic film can be applied as a solution of a film-forming material and a solvent. A swab, applicator tip, or spray method of application can be used. When the solvent evaporates, the film is formed providing the tape occlusion. For example, a solution of the film-former collodion dissolved in the solvent acetone can be used. When the acetone evaporates, a film of collodion will provide tape occlusion. In addition, if desired, a tape can be placed over the collodion film.

If desired, the anthralin can be dissolved along with the film-former in the solvent. Then, when the solvent evaporates, the anthralin is present in the tape that provides the tape occlusion.

Another form of administration of anthralin for treating warts in an environment of tape occlusion is the use of a foam-containing tape or film. Pores or interstitial spaces in the foam can be loaded with anthralin particles. The foam can have an adhesive layer for adhering the foam to skin. If the foam is porous, an outer non-porous layer can be provided on the back of the foam to enhance tape occlusion. A suitable foam tape that can be loaded with anthralin particles, or particles containing anthralin and a stabilizing amount of salicylic acid is Microfoam Surgical Tape(TM), made by the 3M Company, St. Paul, Minn. 55144. Other suitable tapes have ridges and pores but do not contain a foam. With such a tape, particles containing anthralin can be loaded behind the ridges and pores. Then a non-porous tape can be provided as a backing layer. The combination of the porous tape, the particles containing anthralin, and the non-porous backing tape form a slow-release, anthralin-releasing wafer. The non-porous backing tape can have a portion extending beyond the anthralin-containing particles and the porous layer. This portion can include a quantity of adhesive for facilitating adhesion of the wafer to the skin of a user peripheral to warts being treated. A suitable porous tape for this form of anthralin administration with tape occlusion can be the tape known as Transpore(TM), by the 3M Company, St. Paul, Minn. 55144.

A slow-release, anthralin-releasing wafer can also be made by using a porous foam, a quantity of anthralin-containing particles placed behind the porous foam, and a non-porous backing layer placed behind the anthralin-containing particles. The non-porous backing layer can have a portion extending beyond the anthralin-containing particles and the porous layer. This portion can include a quantity of adhesive for facilitating adhesion of the wafer to the skin of a user peripheral to warts being treated.

Yet another carrier for the anthralin can be an aqueous solution that has the ability to gel in the presence of an cation. More specifically, anthralin can be mixed with a quantity of Gelrite (TM) which is a purified anionic heteropolysaccharide derived from gellan gum. An aqueous solution Gelrite (TM) in the presence of a cation has the ability to gel. Upon contact with the salts present on a patients skin, the Gelrite (TM) can gel. Gelrite (TM) is made by Merck & Co., Inc., Whitehouse Station, N.J.

Further in accordance with the invention, a method is provided for treating a wart comprising the steps of: obtaining a composition containing anthralin in a carrier together with a non-therapeutic amount of salicylic acid; applying the composition directly on the wart; providing an occluding environment for the wart. The occluding environment can be provided by a quantity of an adhesive tape.

Still further in accordance with the invention, a kit can be provided which contains a composition containing anthralin, in either a tube or small bottle having an applicator tip, along with a waterproof adhesive tape or other suitable occlusion device. The tape can be a roll of tape or premeasured geometrical shapes and sizes for occlusion.

Whenever an anthralin is employed, a stabilizing (acidifying) amount of salicylic acid can also be employed. As mentioned above, the amount of salicylic acid used is less than a therapeutic amount; that is a non-therapeutic amount of salicylic acid is employed. More specifically, a stabilizing (acidifying) amount of salicylic acid is less than 12% by weight of salicylic acid. Even more specifically, a stabilizing (acidifying) amount of salicylic acid is less than 5% by weight of salicylic acid.

Aside from using the generic anthralin per se, other anthralins can be employed. That is, derivatives or analogs of generic anthralin can be employed. As mentioned hereinabove, derivatives or analogs of anthralin are disclosed in the following U.S. Pat. Nos. 4,465,688; 4,696,941; and 4,866,095. In this respect, for their disclosure of anthralin derivatives or analogs, U.S. Pat. Nos. 4,465,688, 4,696,941, and 4,866,095 are incorporated herein by reference. For purposes of the present invention the term anthralin is deemed to include the derivatives or analogs of anthralin disclosed in U.S. Pat. Nos. 4,465,688, 4,696,941, and 4,866,095.

Although a knowledge of the mechanism of operation of the anthralin in treating the warts is not necessary for instructing a person with ordinary skill in the art as to how to make and use the invention, a suggested explanation may be of value. However, it is understood that the inventors are not bound by any theoretical explanation as to why the compositions and the methods of the invention are efficacious in treating warts.

It is thought that the use of anthralin with tape occlusion in treating warts, in accordance with the invention, elicits an immune response in the patient localized at the warts. The patient's immune response helps destroy the virus infected cells that are present in the warts and helps in preventing further virus and wart growth.

It is understood that the method of the invention can be used to treat a wide variety of warts which are found on human skin and which are caused by the human papilloma virus (HPV). For example, the method of the invention can be used to treat the following types of warts: common warts (verruca vulgaris), plantar warts, palmar warts, planar warts (verruca plana), mosaic warts, and venereal warts (condyloma accuminatum).

BRIEF DESCRIPTION OF THE DRAWINGS

The invention will be better understood and the above objects as well as objects other than those set forth above will become more apparent after a study of the following detailed description thereof. Such description makes reference to the accompanying drawing wherein.

DETAILED DESCRIPTION OF PREFERRED EMBODIMENTS

Treatment of Eight Patients

Figure 1:
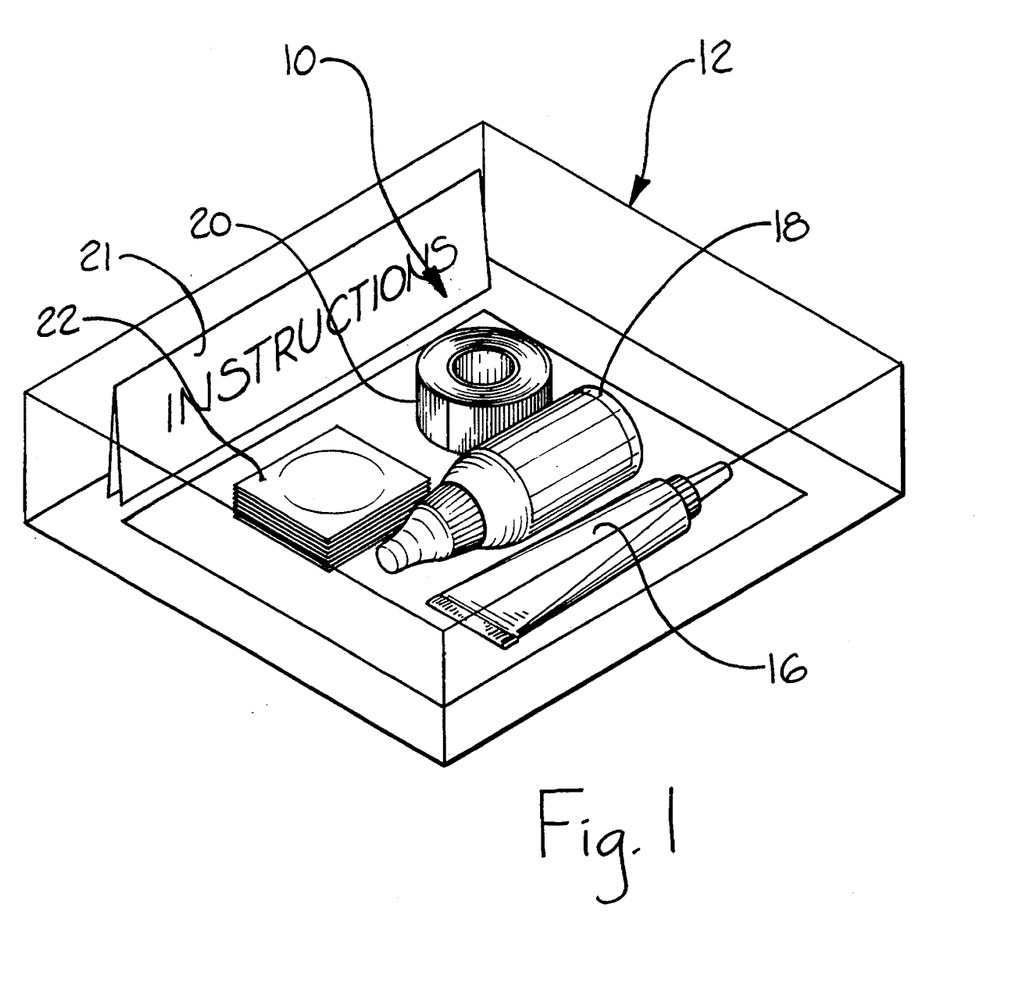
FIG. 1 is a perspective view of a kit that is provided in accordance with the principles of the invention.
Figures 2, 3, 4:
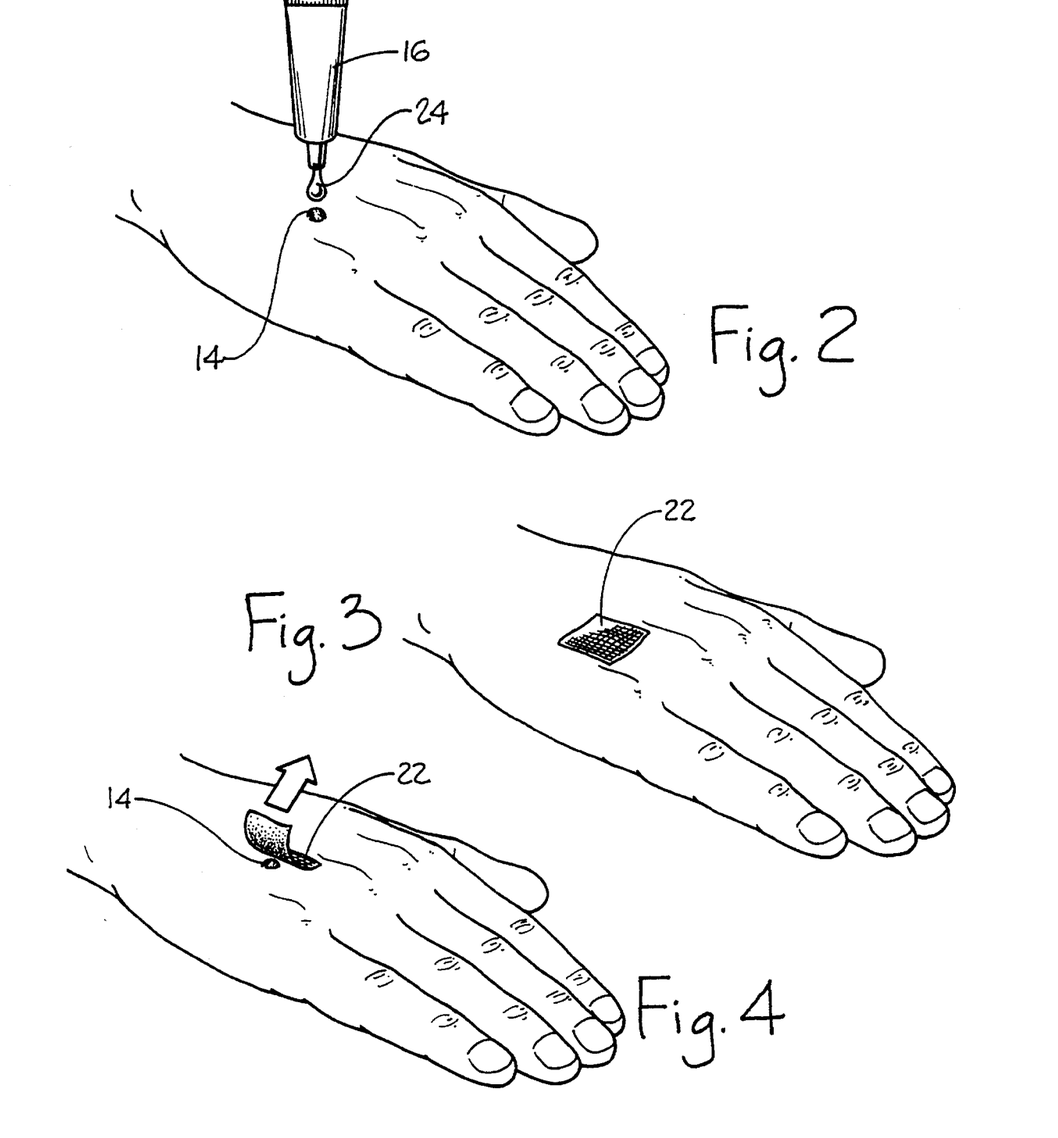
FIG. 2 is a perspective view of a drop of an anthralin-containing composition being dispensed from a tube from the kit shown in FIG. 1 for contact with a wart on the back of a human hand.
FIG. 3 is a perspective view of the hand shown in FIG. 2 with an occluding device placed over the anthralin-treated wart.
FIG. 4 is a perspective view of the occluding device being removed from the hand shown in FIG. 3.
Figure 5:
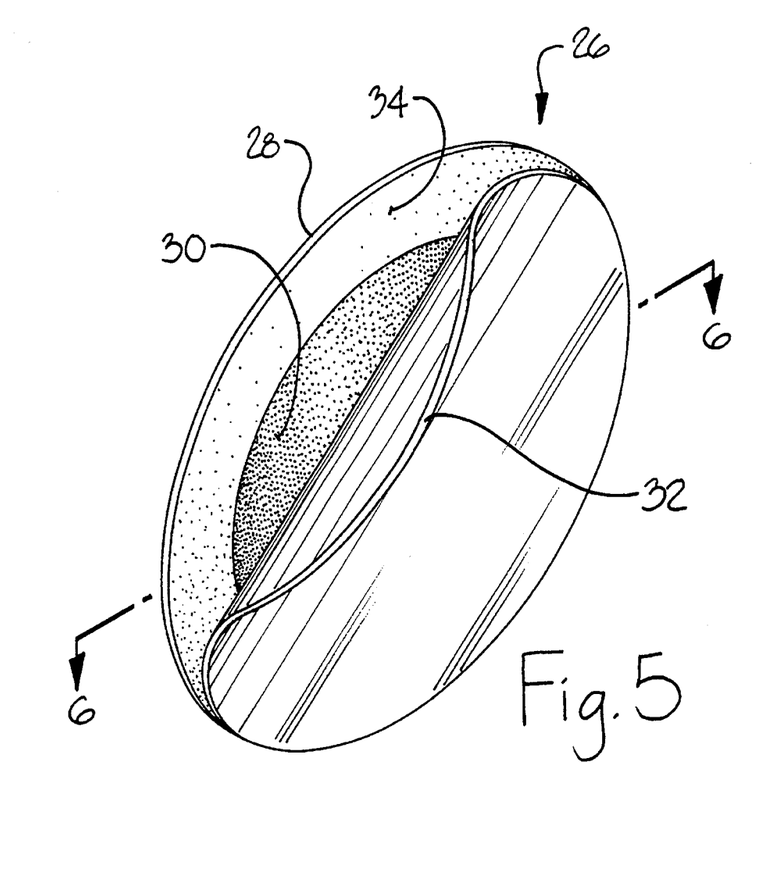
FIG. 5 is a bottom view of another device for carrying out the principles of the invention.
Figure 6:
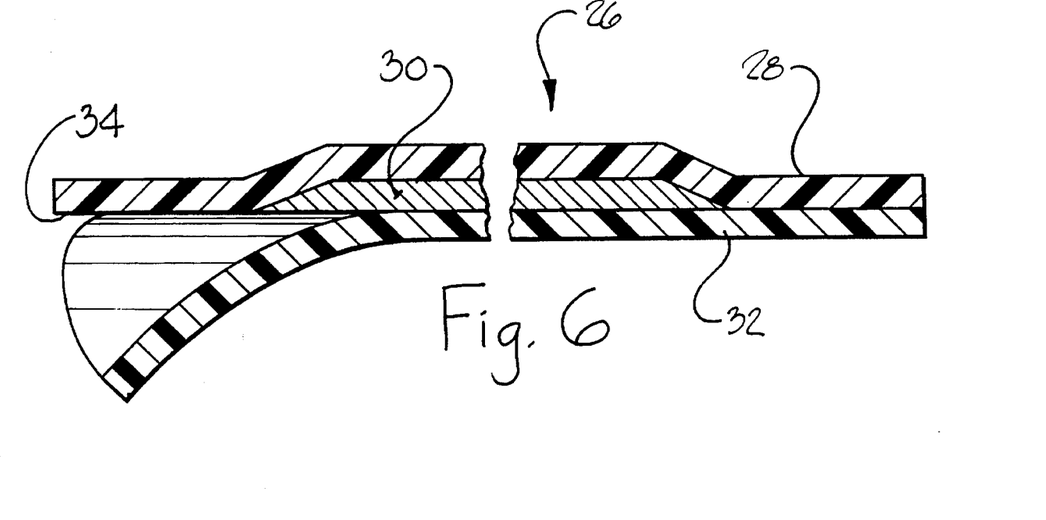
FIG. 6 is a cross-sectional view of the device shown in FIG. 5 taken along line 6—6 in FIG. 5.

Eight patients having warts have been successfully treated with 1 percent anthralin cream (specifically 1.0 percent Drithocreme (TM), a product of Dermik Labs, Inc.) with occlusion conditions under adhesive tape, and the case histories are described as follows.

Patient number one was a 28 year old female who was seen for treatment of mosaic wart virus infection of her right plantar (bottom surface) foot and right first toe. She had previously been treated with salicylic acid with adhesive occlusion overnight, cryosurgery (liquid nitrogen therapy), and carbon dioxide laser surgery without clearing of her warts. Since other conventional therapy had failed, the patient after consent, started 1.0 percent anthralin cream (specifically-1.0 percent Drithocreme (TM), product of Dermik Labs, Inc.) under occlusion with adhesive tape each night and removal in the morning. This was repeated each night. The patient was seen one month later. The warts on her right first toe were cleared and approximately 10 percent of the warts were left on her right foot. The patient was instructed to use the topical 1.0 percent anthralin for 2 weeks longer. The patient returned 5 weeks later or 9 weeks from baseline and was clinically clear of her warts. There was no recurrence of the right plantar foot warts at this follow-up visit.

Patient number two was an 11 year old female who first presented to an inventor at age 10 for a giant cluster of warts on her right medial plantar foot. She had been previously treated by her mother with over-the-counter salicylic acid, then by an inventor with both cantharidin and salicylic acid with adhesive tape occlusion each night and with cryosurgery without improvement. After parental consent the patient was treated with 1.0 percent anthralin cream with adhesive tape occlusion eight hours nightly with removal in the morning, for a period of 2 weeks. At the follow-up appointment 2 weeks later the warts were only 20 percent decreased from baseline exam. Upon further questioning to the mother she had not been using adhesive occlusion, she had applied gauze between the 1.0 percent anthralin cream and the adhesive tape. The mother and patient were re-educated on the use of 1.0 percent anthralin cream with adhesive tape occlusion 8 hours each night. Three weeks later, or 5 weeks from baseline, the warts were clinically cleared.

Patient number three was a 44 year old female who presented to an inventor at age 43 for treatment of a wart on her right second finger. She was treated with cryosurgery and then excisional surgery. The wart recurred, and the patient was treated approximately 1 year later, after consent, with 1.0 percent anthralin cream under adhesive tape occlusion and was seen 3 weeks later. The wart was 50 percent improved. This wart infection was a resistant cluster of warts. The patient was seen 4 weeks later after 7 weeks of continuous use of the above therapy, and was found to be 75 percent clear of the wart cluster. The patient continued 1.0 percent anthralin cream another 2 weeks and was seen again. The warts were 95 percent gone. The patient continued this therapy another 4 weeks and was clinically clear of warts. This represented a time from baseline to clearing of 13 weeks.

Patient number four was seen at age 36 by an inventor for the treatment of resistant left plantar foot warts and a left fourth toe wart. He was status post cryosurgical treatment, carbon dioxide laser surgery, and excisional surgery with recurrence of the warts. The inventor first attempted to treat the patient with dinitrochlorobenzene (DNCB) sensitization to induce a contact allergy and clear the warts from the immunologic reaction. However, 7 weeks later the patient was seen and had no clearing of the warts and no response to DNCB. Approximately 2 and one half weeks later via phone the patient indicated there was no change in his warts and no reaction to DNCB.

Therefore the patient failed 9 and one half weeks of DNCB therapy. The patient after consent was started on 1.0 percent anthralin cream under adhesive tape occlusion nightly with removal in the morning. The patient was seen 2 weeks later and was noted to have at least 50 percent diminution in his left plantar foot and left fourth toe warts. Approximately 3 weeks later the patient returned and 75 percent of the left plantar foot wart cluster was gone, and the left fourth toe wart was completely clear. The patient was treated another 3 weeks on 1.0 percent anthralin cream under adhesive tape occlusion and was noted to have complete clearing of his left plantar foot wart and the left fourth toe wart was still clear.

After approximately 8 weeks using 1.0 percent anthralin cream under adhesive occlusion his warts which were previously refractory to multiple treatment modalities were now clear.

Patient number five was a 13 year old female who had a refractory wart on her left elbow. She had been previously treated with topical cantharidin, oral vitamin A, DNCB and then when these treatments failed she was started after parental consent on 1.0 percent anthralin cream with adhesive tape occlusion nightly, with removal in the morning. Three weeks later she was completely clear of the refractory wart on her left elbow.

Patient number six was an 11 year old female who had a refractory wart on her left foot. She had been previously treated with cantharidin, and topical salicylic acid under adhesive occlusion. Since the above two regimens failed after parental consent she was started on 1.0 percent topical anthralin cream under adhesive tape occlusion. Two weeks later the resistant wart was clear.

Patient number seven was a 19 year old female who had a resistant wart on her right foot. She had been previously treated with cryosurgery, topical salicylic acid under occlusion, and cantharidin without success. She was placed on topical 1.0 percent anthralin cream under adhesive tape occlusion nightly with removal in the morning, after consent was obtained. Approximately two and one half weeks later her wart was clear.

Patient eight was a 60 year old male who had a refractory mosaic wart virus cluster on his left plantar foot. He was treated with topical salicylic acid with adhesive tape occlusion, cryosurgery, DNCB, then after all previous methods had failed, and after consent he was started on topical 1.0 percent anthralin cream under adhesive occlusion eight hours each day. Approximately two weeks later 50 percent of the wart cluster was cleared, he was continued on this therapy. Four weeks later his warts on his left plantar foot were cleared. This was 6 weeks after starting topical 1.0 percent anthralin under adhesive occlusion for 8 hours each day.

Then 6 weeks later the patient complained of a new wart adjacent to his previous wart site. This wart was excised. Due to the proximity of the previous wart the inventor is inclined to call this wart a recurrence.

For convenience, the results of treating the eight patients described above are presented in the following "Patient Treatment Table."

| Patient Treatment Table | | | | |
|---|---|---|---|---|
| Treating agent: | 1.0 percent anthralin cream, specifically 1.0 percent Drithocreme ™, a product of Dermik Labs, Inc. | | | |
| Treatment conditions: | under adhesive tape occlusion | | | |

| Patient | Sex | Age of patient | Location of Wart(s) | Status After End of Treatment | Time between Baseline Exam and end of Treatment |
|---|---|---|---|---|---|
| 1 | F | 28 | foot, toe | clear | 9 weeks |
| 2 | F | 11 | foot | clear | 5 weeks |
| 3 | F | 44 | finger | clear | 13 weeks |
| 4 | M | 36 | foot, toe | clear | 8 weeks |
| 5 | F | 13 | elbow | clear | 3 weeks |
| 6 | F | 11 | foot | clear | 2 weeks |
| 7 | F | 19 | foot | clear | 2.5 weeks |
| 8[1] | M | 60 | foot | clear[1] | 6 weeks |

Footnotes:
[1]Six weeks after clearing of original wart, a new wart appeared adjacent to site of the original wart and may be deemed to be a recurrence.

Other modes of administration of anthralin for treating warts are contemplated. For example, it is contemplated that the anthralin can be administered to the warts by intralesional injection. In other words, the use of a depot or deposition method of treating warts with anthralin is also contemplated.

It is known in the prior art to treat common warts by intralesional injection of bleomycin. It is also known in the prior art to treat venereal warts by intralesional injection of podophyllotoxin or interferon. However, the use of intralesional injection of anthralin to treat warts is not contemplated. Moreover, the intralesional injection of anthralin accompanied by tape occlusion is not contemplated in the prior art.

Turning back to a discussion of the method of the invention, more specifically, an injectable solution/suspension containing anthralin is first prepared. In doing so, a quantity of bacteriostatic saline (NaCl for injection) is obtained. This bacteriostatic saline is a drug diluent and contains approximately 0.9% by weight NaCl, benzyl alcohol as a preservative, and water for injection adjusted for desired pH (substantially neutral) with NaOH or HCl as necessary. Approximately 5 grams of anthralin are dissolved and/or suspended in 100 ml of the bacteriostatic saline.

After preparing the injectable anthralin, a wart is selected for treatment. Prior to treating with the injectable anthralin composition, the wart may be pretreated. One way of pretreating the wart is to pare it or scrape it to remove or separate surface material. Another way of pretreating the wart is to score the wart with a small gauge needle, e.g. No. 21 or No. 27 gauge, in a cross-hatch pattern, like a tic-tac-toe grid. A generic term that includes paring, scraping, and scoring is debriding.

Then the selected wart, whether or not pretreated, is injected with the injectable anthralin composition. A fine gauge needle such as a No. 27 or No. 30 needle can be used. The injection can be superficial. This is especially desirable for pretreated warts. Also, the injection can be relatively deep. This is especially desirable for warts that have not been pretreated. Also, if desired, both superficial injections and deep injections can be carried out on the same wart.

It is contemplated that each injection treatment of a wart will administer from 0.05 to 0.2 cc of the injectable anthralin composition per wart.

It is contemplated that patients having warts that are debrided and then treated with superficial injection can be treated at at least 24 hour intervals, e.g. 3 times per week in a doctor's office. After each treatment and between treatments, a tape is placed over the treated wart to permit tape occlusion in accordance with the invention.

Alternatively, with superficial intralesional injection of an anthralin into a wart, tape occlusion need not be employed.

It is contemplated that patients who are treated with deep injection of the injectable anthralin composition can be treated once a week; that is the predetermined period of time between deep injections is contemplated to be approximately 5–7 days. Tape occlusion is applied to the injection-treated warts between treatments.

Alternatively, with deep intralesional injection of an anthralin into a wart, tape occlusion need not be employed. Stated more generally, it is contemplated that intralesional injection of anthralin into warts can be carried out without using tape occlusion between treatments.

Injection treatments are continued until a desired level of wart resolution is attained.

It is also contemplated that prior to topical application of an anthralin-containing composition to a wart, the wart can be pretreated by debriding the wart. The debriding of the wart facilitates penetration of the anthralin-containing composition into the wart. For example, a wart can be scored by a sharp needle, and an anthralin-containing composition can be added dropwise onto the scored wart. Then, the scored and anthralin-treated wart is covered by a tape for carrying out tape occlusion.

EMBODIMENT IN THE DRAWING

With reference to FIG. 1, a kit 10 is provided which includes a package 12 (which may be a box) for housing a container which contains a quantity of an anthralin-containing composition for treating a wart 14 (shown in FIG. 2). The kit 10 also includes means for providing an occluding environment for the wart 14 in accordance with the principles of the invention.

More specifically, the kit 10 can include an anthralin-containing composition in a tube 16 and/or in a bottle 18 which may contain an applicator tip. The anthralin-containing composition can also be in a sprayable formulation and be sprayed by a spray dispenser.

To provide an occluding environment for a wart, the kit 10 can also include a roll of adhesive tape 20 and/or a stack of adhesive patches 22. An instruction sheet 21 can also be provided in the kit 10.

Generally, for a kit, one or more specific anthralin-containing compositions and one or more specific elements for providing an occluding environment are provided.

In FIG. 2, a drop 24 of anthralin-containing composition is being dispensed from a tube 16 onto the wart 14.

In FIG. 3, a patch 22 has been placed over the wart 14 and adjacent peripheral skin to provide an occluding environment for the anthralin-treated wart for a predetermined period of time.

In FIG. 4, after the predetermined period of time, the patch 22 is being removed from the wart 14 and the adjacent skin areas.

In FIGS. 5 and 6, another device 26 is provided for carrying out the principles of the invention. The device 26 includes an outermost flexible occlusion-providing layer 28 which contains an adhesive coating on its inner side, a flexible layer 30 containing a quantity of anthralin attached to the occlusion-providing layer 28, and a peel off strip 32 attached to the occlusion-providing layer 28. The flexible anthralin-containing layer 30 can be a foam tape loaded with anthralin particles, or particles containing anthralin and a stabilizing amount of salicylic acid. A suitable foam tape for this purpose is Microfoam Surgical Tape(TM), made by the 3M Company, St. Paul, Minn. 55144.

To use the device 26, the peel off strip 32 is removed, the flexible layer 30 containing the anthralin is placed on top of the wart 14, and the exposed adhesive-containing portion 34 of the occlusion-providing layer 28 is placed on areas of skin peripheral to the wart 14. The occlusion-providing layer 28 provides occlusion to the anthralin-treated wart 14 for a predetermined period of time until it is removed.

Formulations Containing Anthralin

A large number of compositions containing an anthralin can be used topically with tape occlusion to treat warts. The following formulations for compositions containing an anthralin and a pharmaceutical carrier may be used topically with tape occlusion in accordance with the principles of the invention.

EXAMPLE 1

In an article by M. Whitehead entitled "Pharmaceutical formulations of anthralin", in the British Journal of Dermatology, Vol. 105 (suppl 20), pages 28–32 (1981), there are disclosures of pharmaceutical formulations of anthralin. In the Whitehead article, there is a disclosure that anthralin is soluble in a pharmaceutical carrier of a 50% paraffin paste only to the extent of 0.1%. In an anthralin formulation in a 50% paraffin paste that exceeds 0.1% anthralin, the anthralin present above 0.1% is in a suspension. The Whitehead article also teaches that salicylic acid in the pharmaceutical carrier serves as an acidifying agent for anthralin compositions which decompose rapidly in alkaline conditions. The article also teaches that when the pharmaceutical carrier for anthralin is an emulsion of white soft paraffin and water, the oxygen in the water may degrade the anthralin. Ascorbic acid is added as an antioxidant. Thus, the emulsion, which is a cream, contains droplets of oil which contain acidulated anthralin, and the oil droplets are surrounded by an aqueous phase which contains the antioxidant ascorbic acid. Thus, the anthralin-containing oil droplets are surrounded by oxygen-free water.

EXAMPLE 2

As mentioned above, Drithocreme(TM) marketed by Dermik Labs is comprised of anthralin (0.1%, 0.25%, 0.5%, or 1%) in a pharmaceutical carrier comprised of a base of white petrolatum, sodium lauryl sulfate, cetostearyl alcohol, ascorbic acid, salicylic acid, chlorocresol, and purified water. In view of the teachings in the Whitehead article, the respective functions of the anthralin and the pharmaceutical carrier components of the Drithocreme (TM) listed above can be deduced as follows. Anthralin (0.1%, 0.25%, 0.5%, or 1%) is the active ingredient. In the pharmaceutical carrier, white petrolatum is a solvent for and suspending agent for anthralin; sodium lauryl sulfate and cetostearyl alcohol are surfactants; ascorbic acid is an antioxidant; salicylic acid is an oil-soluble acid; chlorocresol is an antibacterial; and purified water is a suspending medium that works with the white petrolatum and the surfactants to form the cream carrier. The surfactants help maintain the emulsion of the oil droplets in the aqueous medium.

EXAMPLE 3

Alternative formulations of an anthralin cream also include the anthralin active ingredient and the pharmaceutical carrier which includes an oil base for dissolving and suspending the anthralin, an oil-soluble acidifying agent, an aqueous medium, and a water-soluble antioxidant. In addition, alternative anthralin cream formulations may also include a surfactant for stabilizing the oil-in-water emulsion.

EXAMPLE 4

The Whitehead article also teaches other anthralin-containing formulations. For example, an anthralin ointment employs a pharmaceutical carrier described in the British Pharmacopoeia as Lassar's paste. This carrier includes 240 g. of zinc oxide finely sifted, 20 g. of salicylic acid finely sifted, 240 g. of starch finely sifted, and 500 g. of white soft paraffin. Anthralin ointments containing the Lassar's paste can include anthralin in concentrations ranging from 0.5% to 5.0%. It is noted that the percentage of salicylic acid in a Lassar's paste based ointment is approximately 2.0% by weight.

EXAMPLE 5

In chapter 7, by Ashton et al entitled "Anthralin Therapy of Psoriasis" in the book Practical Psoriasis Therapy, by Lowe, published by Yearbook Medical Publishers, Chicago, Ill., 1986, pages 59–71, a number of anthralin containing formulations are described for treating psoriasis. For example, on page 59, an ointment containing anthralin is provided by dissolving anthralin in chloroform and then adding the chloroform/anthralin solution to the pharmaceutical carrier petrolatum. After mixing, the chloroform is allowed to evaporate off, leaving the suspension of anthralin in petrolatum.

EXAMPLE 6

A composition containing anthralin for treating warts by tape occlusion is obtained as follows.

Mix the following ingredients in the amounts specified.

| Ingredient | Weight Percent |
| --- | --- |
| Ethyl alcohol | 41.5 |
| Laureth-4 | 0.5 |
| Isopropyl alcohol | 6.0 |
| anthralin | 1.0 |
| Purified water | balance |

Ascorbic acid can be used to adjust the pH to a desired level and to serve as an antioxidant.

The composition in this example contains approximately 1% anthralin. Other suitable compositions can be made in accordance with this example which include anthralin in the following percentages: 0.5%, 1%, 3%, 4%, and 5%.

EXAMPLE 7

A composition containing anthralin for treating warts by tape occlusion is obtained as follows.

Mix the following ingredients in the amounts specified.

| Ingredient | Weight Percent |
| --- | --- |
| Ethyl alcohol | 72.2 |
| Propylene glycol | 26.8 |
| anthralin | 1.0 |

The composition in this example contains approximately 1% anthralin.

Other topical dermatological compositions are presented below.

EXAMPLE 8

A formulation employing a water soluble gel as a carrier is obtained as follows. More details of the gel carrier are described in U.S. Pat. No. 4,837,378, incorporated herein by reference.

A 30 kilogram batch of a composition of the present invention containing anthralin (as 0.75% by weight) is prepared as follows. 180grams of Carbopol 940 (TM) (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 300 grams of anthralin dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Ascorbic acid, 1 gram, is added as an anti-oxidant for the anthralin. Distilled water is then added to give the desired 30 kilogram final weight. The NaOH and water are thoroughly mixed into a viscous gel. Other suitable compositions can be made in accordance with this example which include anthralin in the following percentages: 0.5%, 2%, 3%, 4%, 5%, and 10%.

EXAMPLE 9

Another composition containing anthralin for treating warts by tape occlusion is obtained by mixing the following ingredients in suitable amounts: allantoin, carbomer 934P, methylparaben, polyethylene glycol 400, propylene glycol, sodium hydroxide, ascorbic acid, purified water and anthralin.

EXAMPLE 10

A composition containing anthralin for treating warts by tape occlusion is obtained as follows.

Mix the following ingredients in the amounts specified.

| Ingredient | Weight Percent |
|---|---|
| Ethyl alcohol | 48.0 |
| Laureth-4 | 0.5 |
| Isopropyl alcohol | 4.0 |
| Propylene glycol | 10.0 |
| anthralin | 1.0 |
| Purified water | balance |

Ascorbic acid can be used to adjust the pH to a desired level and to serve as an anti-oxidant.

The composition in this example contains approximately 1% anthralin. Other suitable compositions can be made in accordance with this example which include anthralin in the following percentages: 0.5%, 2%, 3%, 4%, 5%, and 10%.

EXAMPLE 11

A lotion composition is obtained as follows. Mix the following ingredients in the amounts specified.

| Ingredient | Weight Percent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 71.8 |
| Propylene glycol | 4 |
| Acetone | 10 |
| Dioctyl sodium sulphosuccinate | 0.1 |
| anthralin | 1 | other suitable compositions can be made in accordance with this example which include anthralin in the following percentages: 0.5%, 2%, 3%, 4%, 5%, and 10%.

EXAMPLE 12

A cream composition is obtained as follows. Mix the following ingredientsin the amounts specified.

| Ingredient | Weight Percent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 62.30 |
| Propylene glycol | 4 |
| Acetone | 11 |

-continued

| Ingredient | Weight Percent |
|---|---|
| Dioctyl sodium sulphosuccinate | 0.1 |
| anthralin | 1 |

Other suitable compositions can be made in accordance with this example which include in the following percentages: 0.5%, 2%, 4%, 5%, and 10%.

EXAMPLE 13

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 62.30 |
| Propylene glycol | 4 |
| Acetone | 11 |
| Dioctyl sodium sulphosuccinate | 0.1 |
| anthralin | 1 |

Other suitable compositions can be made in accordance with this example which include anthralin in the following percentages: 0.5%, 2%, 4%, 5%, and 10%.

EXAMPLE 14

A gel composition is obtained as follows. Mix the following ingredients in the amounts specified.

| Ingredient | Weight Percent |
|---|---|
| Water, deionized or distilled | 55.65 |
| Butylated hydroxyanisole | 0.10 |
| Dioctyl sodium sulphosuccinate | 1 |
| Colloidal Bentonite | 3.5 |
| Carboxy vinyl polymer (acid form) | 1 |
| Ethyl alcohol | 36 |
| Diisopropanolamine | 0.75 |
| anthralin | 1 |

Other suitable compositions can be made in accordance with this example which include anthralin in the following percentages: 0.5%, 2%, 4%, 5%, and 10%.

EXAMPLE 15

A lotion is obtained by mixing the following ingredients in suitable amounts: anthralin (approximately 1% by weight); and a pharmaceutical carrier which includes isopropyl alcohol (approximately 80% by weight), purified water (approximately 9% by weight), and propylene glycol (approximately 10% by weight).

EXAMPLE 16

An oil-in-water emulsion containing anthralin in ointment form is obtained as follows.

Part A is comprised of a 1.67% aqueous solution of anthralin.

Part B is an ointment base comprised of:

| Ingredient | Weight Percent |
| --- | --- |
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 1% anthralin. Other suitable compositions can be made in accordance with this example which include anthralin in the following percentages: 0.5%, 2%, 3%, 4%, 5%, and 10%.

EXAMPLE 17

A mineral-oil-based anthralin ointment is obtained as follows.

Part A is comprised of a 3.33% aqueous solution/suspension of anthralin.

Part B is an ointment base comprised of:

| Ingredient | Parts |
| --- | --- |
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 1% anthralin. Other suitable compositions can be made in accordance with this example which include anthralin in the following percentages: 0.5%, 2%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 1 gram of anthralin (30 g.×3.33%) and approximately 28 grams of water (30 g.×93.34%) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 18

There is a well known and commercially available liquid-absorbed wipe known as Erycette (TM) which is a 2% erythromycin topical solution absorbed into a wipe material comprised of fibrous material. These wipes are packaged in individually sealed aluminum foil packets called Pledgets. As disclosed on the Pledget package, each milliliter of liquid absorbed on the cloth wipe contains 20 mgm erythromycin base in a vehicle consisting of alcohol (66%) and propylene glycol and may contain citric acid to adjust pH. Each pledget is filled to contain 0.8 ml. of solution.

Now in accordance with the principles of the present invention, a 1% anthralin topical solution is prepared and is absorbed into a quantity of an absorbent wipe material comprised of fibrous material such as cloth, paper, or synthetic fibers. Alternatively, an open-cell foam absorbent material can be used. The wipes are packaged in individually sealed aluminum foil packets. Each milliliter of liquid absorbed on the wipe contains 10 mgm anthralin base in a vehicle consisting of alcohol (66%) and propylene glycol and may contain ascorbic acid to adjust pH and serve as an anti-oxidant. Each individual wipe is filled to contain 0.8 ml. of solution.

A variety of strengths can be used for the anthralin solution in the liquid-absorbed wipe. For example, the anthralin can be present in a range spanning 0.5–10% by weight. A variety of liquid carriers and a variety of strengths of the liquid carriers can be used for the anthralin. For example, the carrier can contain a quantity of water in addition to the alcohol and propylene glycol. Moreover, a carrier can contain a blend of water, ethyl alcohol, and isopropyl alcohol such as found in the carrier known as "Neutrogena Vehicle N (mild)" made by Neutrogena Dermatologics Division of Neutrogena Corporation, Los Angeles Corporation. A wide range of proportions of individual carrier ingredients can be employed.

EXAMPLE 19

In this example, anthralin is prepared for topical administration with liposomes. Methods of preparing liposomes containing active ingredients are disclosed in U.S. Pat. No. 4,673,567, incorporated herein by reference. More specifically, Examples 1 and 4 (which is for the cephalosporin cefalexin) in U.S. Pat. No. 4,673,567 are adapted herein for use with the anthralin.

More specifically, 700 mg of D,L-dipalmitoylphosphatidyl choline is dissolved in chloroform in a round-bottom flask. The chloroform is removed by a rotary-evaporator to form a thin layer of phospholipid on the inner wall of the round-bottom flask. The phospholipid is dried sufficiently under reduced pressure, to which 25 ml of water is added. The mixture is shaken by hand at 50 degrees Centigrade for about 7 minutes to give a dispersion of liposomes (multilamellar vesicles, MLV). The dispersion is frozen by the used of dry ice/acetone and dried by vacuum lyophilization. The powder obtained is collected and placed in a tube for centrifugal separation. A solution of anthralin (1% anthralin by weight) is dissolved in purified water in the tube; and 2-fold diluted aqueous isotonic sodium chloride solution and 0.02M phosphate buffer are added to the tube. The mixture is dispersed well, then warmed up and kept at 50 degrees Centigrade for five minutes and washed twice with an isotonic phosphate buffer solution (pH 7.4) at room temperature by means of ultra-centrifugal separation. The liposomes, containing the anthralin are dried by lyophilization and blended with purified water for topical administration to treat acne.

The anthralin used can be in a solution in a range of 0.5% to 10% by weight.

The lyophilized powder which contains the anthralin in liposomes can also be used in creams and gels.

EXAMPLE 20

A time-release patch containing anthralin is described below. The making of the time-release patch is adapted from U.S. Pat. No. 4,839,174, incorporated herein by reference, which discloses the making of nicotine patches. More specifically, Example 1 is adapted for use with anthralin. Monolithic patches containing the anthralin are made as follows. A solution of anthralin-loaded Pellethane 2363-80AE is made by mixing Pellethane pellets into tetrahydrofuran, adding anthralin to be 1% by weight anthralin. The mixture is agitated on a bottle roller for three days to form a matrix mixture. A layer of backing material grade 3M-1005 is spread in a petri dish and covered with the matrix mixture. The petri dish is covered, and the matrix is left to cure for 10 days at room temperature to form the time-release, anthralin composition. Patches are cut from the finished matrix. Time-release patches can be made in a variety of sizes to accommodate different anatomic locations to which the patches are applied. The anthralin can be added in a range spanning 0.5% to 20% by weight.

As mentioned above, a carrier for the anthralin can contain a blend of water, ethyl alcohol, and isopropyl alcohol such as found in the carrier known as "Neutrogena Vehicle N (mild)" made by Neutrogena Dermatologics Division of Neutrogena Corporation, Los Angeles Corporation. More generally, however, a broad range of suitable amounts of anthralin and respective carrier ingredients is as follows: the anthralin is present in an amount in a range of 0.5–10% by weight; the ethyl alcohol is present in a range of 35–50% by weight; the laureth-4 is present in a range of 0–1% by weight; the isopropyl alcohol is present in a range of 0–10% by weight; and the water is present in a range of 40–60% by weight.

EXAMPLE 21

A composition of anthralin, a film-forming material, and a solvent is as follows:

| | |
|---|---|
| anthralin | 5.0% by weight |
| salicylic acid | 1.0% by weight |
| acetone (solvent) | 15.0% by weight |
| collodion (film-forming material) | 79.0% by weight |

The composition is applied directly onto the warts. The acetone evaporates, and the collodion forms a film which provides occlusion (film occlusion) for the anthralin stabilized (acidified) by the salicylic acid.

Aside from the compositions which disclose anthralin described hereinabove, numerous other compositions which include anthralin can be employed for treating warts with tape occlusion in accordance with the principles of the present invention. As further examples of suitable compositions containing anthralin, reference is made to the exemplary anthralin-containing compositions disclosed in U.S. Pat. Nos. 4,495,203 and 4,504,494, both by Grollier et al, mentioned hereinabove.

In this respect, U.S. Pat. No. 4,495,203 is incorporated herein by reference, and the anthralin-containing gel compositions for treating the skin that are disclosed in Examples 1–5 in U.S. Pat. No. 4,495,203 are incorporated herein by reference. Furthermore, the percentages of anthralin in these compositions can be altered to be in a range of from 0.50% to 10.0% by weight.

Also, in this respect, U.S. Pat. No. 4,504,494 is incorporated herein by reference, and the anthralin-containing compositions for treating the skin that are disclosed in Examples IV, VII, VIII, XIII, and XIV, in U.S. Pat. No. 4,504,494 are incorporated herein by reference. Furthermore, the percentages of anthralin in these compositions can be altered to be in a range of from 0.50% to 10.0% by weight.

The foregoing description of the invention has been presented for purposes of illustration and description. It is not intended to be exhaustive or to limit the invention to the precise forms disclosed. Obvious modifications or variations of the methods and compositions of the invention are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method of treating a patient having one or more warts, said method comprising the steps of:

(a) applying to a wart an amount of a composition consisting essentially of an anthralin active ingredient in a concentration greater than 0.5% by weight and a pharmaceutical carrier, (b) covering the wart and skin area peripheral to the wart with a tape which provides an occluding environment for the wart, and (c) maintaining the tape in position over the wart and peripheral skin area for a predetermined period of at least one hour, the tape providing an occluding environment for the wart for the predetermined period of time.

2. The method described in claim 1, further including the steps of:

(d) removing the tape after the predetermined period of time, and (e) repeating steps (a) through (d) periodically until a desired level of wart removal has been obtained.

3. The method described in claim 2 wherein steps (a) through (d) are repeated daily until a desired level of wart removal has been obtained.

4. The method described in claim 2 further including the step of debriding the wart after removing the tape after the predetermined period of time and prior to repeating steps (a) through (d).

5. The method described in claim 1 wherein the anthralin and the pharmaceutical carrier are present in a form of an emulsion.

6. The method described in claim 5 wherein the emulsion is a cream.

7. The method described in claim 1 wherein the anthralin and the pharmaceutical carrier are present in a form of an oil-in-water emulsion.

8. The method described in claim 1 wherein the pharmaceutical carrier for the anthralin includes an oil base for dissolving and suspending the anthralin, a non-therapeutic amount of an oil-soluble acidifying/stabilizing agent, an aqueous medium, and a non-therapeutic amount of a water-soluble antioxidant, such that the pharmaceutical carrier and the anthralin are present in an oil-in-water emulsion.

9. The method described in claim 8 wherein, in the pharmaceutical carrier:

the oil base is petrolatum, the oil-soluble acidifying/stabilizing agent is salicylic acid present in an amount less than 5% by weight, the aqueous medium is purified water, and the water-soluble antioxidant is ascorbic acid.

10. The method described in claim 8 wherein the pharmaceutical carrier also includes a surfactant for stabilizing the emulsion.

11. The method described in claim 1 wherein the anthralin is present in a concentration range spanning 0.50%–1.50% by weight.

12. The method described in claim 1 wherein the anthralin is present in a concentration ranging from 0.50%–5.0% by weight.

13. The method described in claim 1 wherein the anthralin is present in a concentration ranging from 0.50%–10.0% by weight.

14. The method described in claim 1 wherein the predetermined time for tape occlusion is at least 4 hours.

15. The method described in claim 1 wherein the predetermined time for tape occlusion is at least 5 hours.

16. The method described in claim 1 wherein the predetermined time for tape occlusion is at least 6 hours.

17. The method described in claim 1 wherein the predetermined time for tape occlusion is in a range spanning 1 to 18 hours.

18. The method described in claim 1 wherein:

the anthralin is present in a concentration of approximately 1 percent by weight; and the predetermined time for tape occlusion is at least 4 hours.

19. The method described in claim 1 wherein the tape used for tape occlusion is an adhesive tape.

20. The method described in claim 1 wherein the tape used for tape occlusion is a plastic film.

21. The method described in claim 1 wherein the tape used for tape occlusion is a plastic film which contains anthralin.

22. The method described in claim 1 wherein the tape used for tape occlusion is a plastic foam tape which contains anthralin.

23. The method described in claim 1 wherein the tape used for tape occlusion is a plastic film which contains anthralin and collodion.

24. The method described in claim 1 wherein the tape used for tape occlusion is a plastic film which contains anthralin, collodion, and salicylic acid in an amount less than 5% by weight.

25. The method described in claim 1 wherein:

anthralin is present in a form of anthralin-containing particles, the pharmaceutical carrier is in a form of a porous layer and a non-porous backing layer, and the anthralin-containing particles are located between the porous layer and the non-porous backing layer.

26. A method of treating a patient having one or more warts, said method comprising the steps of:

(a) applying to a wart an amount of a composition consisting essentially of an anthralin active ingredient in a concentration ranging from 0.50%–10.0% by weight and a pharmaceutical carrier which includes an oil base for dissolving and suspending the anthralin, an oil-soluble acidifying/stabilizing agent, an aqueous medium, and a water-soluble antioxidant, such that the pharmaceutical carrier and the anthralin are an oil-in-water emulsion, (b) covering the wart and skin area peripheral to the wart with an adhesive tape which provides an occluding environment for the wart, and (c) maintaining the tape in position over the wart and peripheral skin area for a predetermined period, the tape providing an occluding environment for the wart for the predetermined period of time.

27. The method described in claim 26, further including the steps of:

(d) removing the tape after the predetermined period of time, and (e) repeating steps (a) through (d) daily until a desired level of wart removal has been obtained.

28. The method described in claim 26 wherein, in the pharmaceutical carrier:

the oil base is petrolatum, the oil-soluble acidifying/stabilizing agent is salicylic acid present in an amount less than 12% by weight, the aqueous medium is purified water, and the water-soluble antioxidant is ascorbic acid.

29. The method described in claim 28 wherein the salicylic acid is present in an amount less than 5% by weight.

30. A method of treating a patient having one or more warts, said method comprising the steps of:

(a) injecting an anthralin-containing composition directly into a wart, (b) covering the wart and skin area peripheral to the wart with a tape, and (c) maintaining the tape in position over the wart and peripheral skin area for a predetermined period, the tape providing an occluding environment for the wart for the predetermined period of time.

31. The method described in claim 30, further including the steps of:

(d) removing the tape after the predetermined period of time, and (e) repeating steps (a) through (d) periodically until a desired level of wart removal has been obtained.

32. The method described in claim 31 further including the step of debriding the wart prior to injecting the anthralin-containing composition.

33. A method of treating a wart comprising the steps of:

obtaining a composition containing anthralin in a carrier together with a non-therapeutic amount of salicylic acid, applying the composition directly on the wart, and providing an occluding environment for the wart with a plastic film.

34. The method described in claim 33 wherein the occluding environment is provided by a quantity of an adhesive tape.

35. A kit for treating a wart, comprising:

an occluding means, and a quantity of an anthralin composition which includes a carrier containing a non-therapeutic amount of salicylic acid, such that anthralin in the composition is applied directly to the wart, and such that the wart is thereafter covered by said occluding means.

36. The kit described in claim 35 wherein said occluding means is a quantity of an adhesive tape.

37. A method of treating a patient having one or more warts, said method comprising the steps of:
   (a) applying to a wart an amount of a composition consisting essentially of an anthralin active ingredient and a pharmaceutical carrier,
   (b) providing an occluding environment for the wart, and
   (c) maintaining the occluding environment for the wart for a period of time of at least one hour.

38. The method of claim 37, further including the steps of:
   (d) removing the occluding environment after the period of time, and
   (e) repeating steps (a) through (d) periodically until a desired level of wart removal has been obtained.

39. A method of treating a patient having one or more warts, said method comprising the steps of:
   (a) applying to a wart an amount of a composition consisting essentially of an anthralin active ingredient and a pharmaceutical carrier,
   (b) providing an occluding environment for the wart, and
   (c) maintaining the occluding environment for the wart.

* * * * *